United States Patent
Buess et al.

(10) Patent No.: US 6,680,272 B2
(45) Date of Patent: Jan. 20, 2004

(54) CATALYSTS AND PROCESSES USING THEM

(75) Inventors: Philippe Buess, Overijse (BE); Raphael Frans Ivo Caers, Edegem (BE); Alfred Frennet, Lasne (BE); Eric Ghenne, Orp-Jauche (BE); Claude Hubert, Wezembeek-Oppem (BE); Norbert Kruse, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 133 days.

(21) Appl. No.: 10/014,693

(22) Filed: Dec. 11, 2001

(65) Prior Publication Data

US 2003/0036573 A1 Feb. 20, 2003

Related U.S. Application Data

(62) Division of application No. 09/509,223, filed as application No. PCT/GB98/02896 on Sep. 25, 1998, now Pat. No. 6,362,239.

(30) Foreign Application Priority Data

Sep. 26, 1997 (GB) ............................................. 9720593

(51) Int. Cl.$^7$ ........................... B01J 31/00; B01J 23/00; B01J 23/58; B01J 23/72
(52) U.S. Cl. ..................... 502/115; 502/104; 502/306; 502/314; 502/328; 502/331
(58) Field of Search ................................ 502/115, 104, 502/306, 314, 328, 331

(56) References Cited

U.S. PATENT DOCUMENTS

| | | | | |
|---|---|---|---|---|
| 3,876,557 A | | 4/1975 | Bland .......................... | 252/466 |
| 3,956,189 A | * | 5/1976 | Warshaw et al. ........... | 252/466 |
| 4,096,080 A | * | 6/1978 | Mollard et al. ........... | 252/62.62 |
| 4,122,110 A | | 10/1978 | Sugier et al. ............. | 260/499.5 |
| 4,291,126 A | | 9/1981 | Sugier et al. ............. | 518/713 |
| 4,477,594 A | | 10/1984 | Greene et al. ............. | 518/700 |
| 4,562,174 A | | 12/1985 | Stiles .......................... | 502/174 |
| 4,659,742 A | | 4/1987 | Courty et al. ............. | 518/713 |

OTHER PUBLICATIONS

Henrici–Olive et al., "The Fischer–Tropsch Synthesis: Molecular Weight Distribution of Primary Products and Reaction Mechanism", *Angew. Chem. Int. Ed. Engl.*/vol. 15 (1976) No. 3, pp. 136–141.

Jing, et al., "Selective Production of $C_2$ and $C_3$ Alcohols from Synthesis Gas", *Journal of Natural Gas Chemistry*, vol. 6, No. 1, (1997), pp. 44–50.

Satterfield, Charles N., "Catalyst Preparation and Manufacture", *Heterogeneous Catalysis in Industrial Practice*, McGraw–Hill, Inc., Second Edition, (1991), p. 107.

* cited by examiner

*Primary Examiner*—J. Parsa
(74) *Attorney, Agent, or Firm*—James Zboray; Catherine L. Bell

(57) ABSTRACT

Co-precipitated CoCuMn and CoCuMg catalysts are used in Fischer-Tropsch synthesis.

26 Claims, No Drawings

CATALYSTS AND PROCESSES USING THEM

CROSS-REFERENCE TO RELATED APPLICATIONS

The present application is a division of application Ser. No. 09/509,223 filed Nov. 17, 2000, now U.S. Pat. No. 6,362,239, which is a U.S. National Stage patent application of PCT application PCT/GB98/02896, filed Sep. 25, 1998, which claims priority to Great Britain application GB 9720593.4, filed Sep. 26, 1997.

BACKGROUND OF THE INVENTION

This invention relates to a process for the manufacture of, inter alia, alcohols and hydrocarbons from syngas, and to catalysts for use in the process. More especially, the invention provides a process in which molecules having two or more, especially four or more, carbon atoms are provided from carbon monoxide and hydrogen.

In Angew. Chem. Int., Ed. Eng., 15 (1976) 136, Henrici-Olivé and Olivé give a review of the early history of the Fischer-Tropsch synthesis and its commercial value. As stated in the article, the synthesis is versatile in that depending on the catalyst, temperature, and pressure, the process may be oriented to yield predominantly gaseous or liquid hydrocarbons, waxes, or alcohols as required, linear α-olefins and linear alcohols being the initial reaction products. Depending on the catalyst and conditions, the predominant products vary. These may be, e.g., linear paraffins and alcohols, with branched isomers and other functionalities also being produced. Many of the products are valuable in themselves but the production of others, for example carbon dioxide, is generally to be avoided as far as possible.

A number of patents, for example U.S. Pat. Nos. 4,122,110, 4,291,126, 4,477,594, 4,562,174, and 4,659,742, describe processes for the manufacture of a mixture of alcohols of a molecular weight range that renders them suitable for addition to gasoline, in which various catalysts, usually containing copper, cobalt, an alkali or alkaline earth metal, and at least one further metallic element, are used.

At present, many fuels and other energy sources are transported over long distances in the form of gases or liquefied gas. Such transport is expensive, not least because of the safety measures necessary, including those relating to high pressures. A process that is efficiently (in terms of overall energy use) able to convert a gaseous energy source to a product that is at least partially liquid at ambient temperature or even up to 40° C., would be valuable, even if moderate pressure were required to maintain the product in liquid form. So also would any process that could efficiently convert an energy source that is readily transportable, e.g., a liquid hydrocarbon or coal, but which when burned is environmentally polluting, e.g., because of its sulphur content, by a step (e.g., syngas manufacture) which would enable the pollutant to be removed, before converting or re-converting it to a liquid organic material. Therefore the higher the weighted mean molecular weight of the product of such processes the more desirable the process.

There remains a need, accordingly, for a process in which the weighted mean of the range of molecular weights of the resulting organic materials is higher than that resulting from prior art processes, and preferably one in which the proportion of carbon dioxide formed is low.

The present invention provides, in a first aspect, a process for the manufacture of organic materials, especially alcohols and olefins, from carbon monoxide and hydrogen which is carried out in the presence of a catalytic composition comprising a higher alcohol synthesis catalyst, at least one metallic element selected from the group consisting of magnesium and manganese, and, optionally, an alkali metal or alkaline earth metal, the catalyst being one obtainable by co-precipitation of its essential component metallic elements as oxalates. As higher alcohol synthesis catalyst there is advantageously used one comprising cobalt and copper, cobalt being the "Fischer-Tropsch" catalyst element and copper the "alcohol" element. It will be understood that in the catalyst the metallic elements may be in elemental form or they may be in the form of compounds, e.g., their oxides, or as mixtures of the metals in elemental form and compounds of the metals. By higher alcohols is meant a mixture of alcohols with molecular weights distributed over a range.

In a second aspect, the invention provides a process for the manufacture of a catalyst which comprises forming a solution of a cobalt salt, a copper salt, and a salt of at least one metal selected from manganese and magnesium, and co-precipitating the metals as oxalates from solution by the addition of oxalate ions.

The solvent is advantageously water, although an organic solvent, e.g., methanol, ethanol, acetone or a propanol or a butanol, may be used, if desired in admixture with water.

BRIEF SUMMARY OF THE INVENTION

In a third aspect, the invention provides a catalyst comprising cobalt, copper, and manganese in atomic ratios of Co:Cu:Mn within the range 1:1 to 10:0.1 to 5. Advantageously, the catalyst contains at most 1% by weight of alkali metal. Advantageously, the ratios are in the range 1:1 to 5:0.15 to 3, more advantageously 1:1 to 5:0.2 to 3, and preferably 1:1 to 5:05 to 3, and most preferably 1:1:0.5 to 1. When the Co:Cu ratio is 1:1, and the Co:Mn ratio is 1:<1, the catalyst is advantageously one obtainable, and preferably obtained, by the second aspect process.

In a fourth aspect, the invention provides a catalyst comprising cobalt, copper, and magnesium in atomic ratios of Co:Cu:Mg within the range 1:1 to 10:0.1 to 10. Advantageously, the catalyst contains at most 1% of alkali metal. Advantageously, the ratios are in the range 1:1 to 10:0.15 to 10, more advantageously 1:3 to 7:0.5 to 5, and preferably about 1:4:2.5. When the Co:Cu ratio is 1:<2, and the Co:Mg ratio is 1:<1.5, the catalyst is advantageously one obtainable, and preferably obtained, by the second aspect process.

In a fifth aspect, the invention further provides a catalyst comprising cobalt, copper, and manganese in atomic ratios of Co:Cu:Mn within the ranges 1:1 to 10:0.1 to 5, or comprising cobalt, copper and magnesium in atomic ratios of 1:1 to 10:0.1 to 10, in which the molar proportion of the total cobalt and copper in the catalyst that is present in a mixed phase is at least 25%, advantageously at least 50%, and preferably at least 65%, and may be up to 95% or more.

In a sixth aspect, the invention provides a process for converting a carbonaceous energy source of a first type, e.g., a gas or liquefied gas, or one that is polluted, i.e., contains undesired components, especially sulphur, which comprises converting the source to synthesis gas (carbon monoxide and hydrogen) and then, in the presence of a catalyst according to the invention, or produced according to the invention, converting the synthesis gas to liquid or liquefiable alcohols and/or olefins. If the source of the first type is polluted, the process comprises removing the pollutant before converting or re-converting the energy source to liquid or liquefiable form.

Advantageously, the process of the second aspect of the invention is used to make the catalysts of the third, fourth, and fifth aspects, and a catalyst of the third, fourth, or fifth aspect is advantageously used in the processes of the first and sixth aspects.

In a modification of the second aspect of the invention, presently not preferred, other low molecular weight organic acids, especially dibasic acids, may be used, if the relevant salts have a $pK_5$ value appropriate to ensure immediate simultaneous precipitation. Oxalic acid is preferred since it readily decomposes without leaving residues.

As indicated above, as higher alcohol synthesis catalyst there is preferably used one in which there are two metallic components, one of which is believed to be primarily responsible for the chain growth of the product, e.g., cobalt, iron, and ruthenium, and the other primarily responsible for alcohol formation, e.g., copper, palladium, rhodium, molybdenum, and chromium, although the invention is not to be regarded as limited by any theoretical considerations. It is believed, although again the invention is not to be regarded as limited by any theoretical considerations, that by co-precipitation of the oxalates of the two metals mixed phase materials are produced resulting in a catalyst with good selectivity to alcohols. This effect is surprising since, although Bland, in U.S. Pat. No. 3,876,557, advocated co-precipitation for nickel-cobalt hydrogenation catalysts, Sugier et al, in U.S. Pat. No. 4,122,110, indicated that the catalytic activity in alcohols production from CO and $H_2$ of a catalyst prepared by precipitation was inferior to that of one obtained by evaporation of the solvent from a citric acid-containing solution.

Again without being bound by theory, it is believed that by the presence of manganese or magnesium in the medium from which the oxalates are co-precipitated the cobalt-copper mixed phase is more highly dispersed in the resulting catalyst, resulting in a greater specific surface area and a higher catalytic activity than in their absence.

In J. Nat. Gas. Chem., (1997), 6(1), 45, Li et al describe a co-precipitated cobalt-copper catalyst onto which has been further precipitated a third metal oxide, to give a catalyst with an atomic ratio of Co:Cu:metal of 1:1:0.12. As third metal there are mentioned, inter lia, manganese and magnesium. The manganese-containing material had good selectivity to $C_2$ and $C_3$ alcohols, that containing magnesium did not. It is believed that the catalyst obtained by the two-stage process described cannot have the advantage of the dispersion of mixed phase material obtained by the preferred three-metal co-precipitation process of the present invention.

As a result of the higher catalytic activity and greater surface area of the catalyst of the invention, it is not necessary to employ a catalyst carrier or support, thereby avoiding the difficulties sometimes posed by a supposedly inert carrier, although the presence of such a support is not outside the scope of the invention. For example, a common catalyst support, alumina, tends to cause formation of some cobalt aluminate in the course of catalyst preparation and use, thereby resulting in loss of activity. Heretofore, zinc has frequently been included in a copper-cobalt catalyst for mitigating this and, while it is within the scope of the invention to include zinc, the invention allows a substantially zinc-free catalyst to be prepared. The invention also provides an unsupported catalyst.

Also, as indicated above, the catalyst may contain, in addition to the higher alcohol synthesis catalytic elements, especially copper and cobalt, and the magnesium or manganese, an alkali or alkaline earth metal, the term "alkaline earth" as used in this specification not including magnesium. The metal may be Li, Na (which is at present not preferred), K (which is preferred), Rb, Cs, Ca, Sr, or Ba, these metals being referred to as promoters. Advantageously, the catalyst contains a total of at most 1% by weight of alkali metal and alkaline earth metal, based on the weight of metal in the catalyst.

The catalyst may, in addition, contain other metals, for example, V, Cr, Mo, Zr, Y, La, Zn, Nb, Re, W, and Ti.

In the first and second aspects of the invention, the catalyst is formed by co-precipitation of the essential metals, which will henceforth by referred to for simplicity as copper, cobalt, and one or both of magnesium and manganese, as oxalates from a solution containing the corresponding ions, each preferably being in the +2 oxidation state. The solution may be in water or an organic solvent, e.g., iso-propanol. The nitrate of each metal is advantageously used since it is readily soluble in water or a suitable polar organic solvent, e.g., isopropanol, ethanol, or acetone, and the nitrate ion is less prone to adsorption on the precipitate than, for example, the chloride or sulphate ion. Rapid and simultaneous pre-cipitation is favoured by vigorous stirring to ensure rapid homogenization of the reaction medium. Advantageously, at most a stoichiometric ratio of oxalate to total metal is employed. Since magnesium oxalate is relatively slowly precipitated below about 40° C. and cobalt oxalate is soluble above about 60° C., a temperature between 40° C. and 60° C. is preferred for the co-precipitation when magnesium is present; if manganese only is present, room temperature solutions may be used. As precipitating agent there is preferably used ammonium oxalate or oxalic acid, advantageously added in the form of a solution, preferably an aqueous solution, or in a polar organic solvent, e.g., iso-propanol, acetone, a butanol, or ethanol. Advantageously, the pH of the resulting liquid phase, if the solvent is aqueous, is within the range of 5 to 7, to ensure immediate and simultaneous oxalate precipitation. It has been found that if an organic solvent is used, a more complete precipitation of the metallic elements is achieved.

The optionally present alkali or alkaline earth metal component may conveniently be incorporated into the catalyst after the co-precipitated material has been filtered, washed, dried and calcined, by adding a solution of the required promoter metal, in the form of a nitrate or other salt to the calcined material using the incipient wetness technique, described in C. N. Satterfield, "Heterogeneous Catalysis in Industrial Practice", 2nd Edition, McGraw-Hill, 1991, at page 107. The strength of the solution is advantageously such as to result in a proportion of the alkali or alkaline earth metal, based on the total weight of catalyst metal, in the region of 0.01 to 1.0%, preferably from 0.05 to 0.2%, most preferably about 0.1%, by weight. It has been found that, although selectivity to alcohol rather than hydrocarbons increases with the proportion of promoter, the proportion of the $CO_2$ produced also increases and, as is apparent from the examples below, this must be taken into account in choosing promoter levels. Although not preferred, introduction of potassium may be effected by precipitation with potassium oxalate.

Conveniently, the co-precipitated material which may be regarded as a catalyst precursor is filtered, washed in distilled water, and dried, for example, at a temperature in the range of from 90° C. to 150° C., advantageously at 105 to 115° C., at atmospheric pressure. Catalyst manufacture is continued by heat treatment, for example, calcination at, for example, 400° C. to 600° C., in air for, for example, from 1 to 5 hours to form the metal oxides. Pretreatment of the catalyst, before reaction, may be carried out, if desired or required, by reduction with hydrogen or hydrogen-rich syngas or other hydrogen-containing gas, at elevated temperature, for example, from 300° C. to 400° C., at atmospheric pressure, resulting typically in the presence of both oxides and metals.

Advantageously, the process of the first aspect is carried out using, as synthesis gas, one having a molar ratio of $H_2$ to CO within the range of from 3:1 to 1:1, preferably from 2.5:1 to 1:1, and most preferably at a ratio between 2.1:1 and 1.5:1. Other species, for example, $C_2H_4$, $C_2H_2$, $CO_2$, $CH_4$, may also be present, if desired.

Advantageously, the reaction is carried out at a temperature within the range of from 200° C. to 350° C., preferably from 220° C. to 260° C. for a catalyst containing manganese and from 250° C. to 290° C. for one containing magnesium.

Advantageously, the reaction is carried out at a pressure within the range of from 10 to 150 bar, preferably from 50 to 100 bar, and conveniently about 60 bar.

Advantageously, the reaction is carried out at a volume hourly space velocity within the range of from 2000 to 9000 $h^{-1}$, i.e., normal volumes of gas per volume of catalyst per hour, preferably from 4000 to 7000 $h^{-1}$, most preferably about 4800 $h^{-1}$.

The reaction is advantageously carried out in such a manner that at most 30%, more advantageously at most 20%, preferably at most 10%, and most preferably at most 5%, of the carbon in the carbon monoxide converted is converted to carbon dioxide.

The reaction may be carried out in a mixed phase reactor, e.g., a slurry reactor with the liquid phase being, for example, a heavy alcohol or hydrocarbon, which may for example be provided by the bottom fraction of the reaction product. Unreacted materials may be recycled; the conversion rate per pass may be varied widely as desired, for example by varying the space velocity.

Referring now more especially to the third, fourth and fifth aspects of the invention, it has been found that the selectivity to alcohols increases with an increase in the proportion of the catalyst that is of mixed phase, i.e., one wherein the cobalt and copper are intimately mixed, apparently at an atomic level. The presence of a mixed phase may be established by observation of temperature-programmed decomposition, TPDec, of the oxalate precursor to the catalyst. A small sample (about 30 mg) is heated at 9° C. per minute under a stream of hydrogen in argon. The outlet gas strewn is analysed by mass spectrometry, determining the proportions of $H_2$, Ar, CO, $CO_2$, $CH_4$ and $H_2O$. The "Carbon amounts", that is, the total quantities of CO, $CO_2$, and $CH_4$, are plotted as a function of temperature, and form peaks as the oxalates decompose. If one or more peaks appear that cannot be attributed to the decomposition either of cobalt- or copper-only-containing phases, it is or are accordingly attributed to one or more mixed phases. The presence of a mixed phase may be confirmed by physical methods e.g., extended X-ray absorption time structure (EXAFS) and energy dispersive spectroscopy (EDS). As used in this specification, the proportion of mixed phase means the ratio of the area of the C (carbon) peak or peaks corresponding to the mixed phase or phases to the sum of all the C peaks in the TPDec.

It has been established that co-precipitation by the second aspect of the invention provides excellent mixing at the precursor stage, i.e., before calcination, contributing to the stability of the catalyst, as indicated by maintenance of catalytic activity. Other, prior art, procedures, e.g., the complexation process, rely on solid-phase reactions during the later stages of calcination and pre-use reduction.

It has been found that a number of compositional factors influence the proportion of mixed phase. In the fourth aspect of the invention, the catalyst of the Co:Cu:Mg system, increasing the ratio of Cu:Co increases the mixed phase proportion, while increasing the ratio of Mg to Cu and Co reduces the mixed phase proportion, at least when the catalyst is made by the process of the second aspect. In the Mg-containing system, however, since an increase in Mg content increases the specific surface area, there is an optimum Mg content, this having been found at the atomic composition Co:Cu:Mg of approximately 1:4:2.5.

The process and composition of the invention make it possible to obtain a mixture of products of the Fischer-Tropsch reaction having a higher mean molecular weight than is obtainable by previously reported work in the field. As set out in detail in the above-mentioned Olivé article, the entire disclosure of which is incorporated herein by reference, the molecular weight distribution of the products of the Fischer-Tropsch process obeys the Schulz-Flory distribution law, which permits prediction of the maximum possible proportion of product within a given molecular weight range for a given mean molecular weight, the law also predicting that the higher the mean molecular weight the broader the spread of the molecular weight. For a given catalyst system, under given conditions, the value of $\alpha$, the probability of chain growth, provides a measure of the mean molecular weight obtainable, a higher $\alpha$ corresponding to a higher mean molecular weight (albeit with a lower theoretically possible maximum proportion of the total product within a given molecular weight range).

In accordance with the distribution law, the correspondence of $\alpha$, the weight percentage of product with a carbon number at and above a given value, and the weight average mean carbon number may be set out as follows:

TABLE 1

| $\alpha$ | % $C_2^+$ alcohol | Mean C No. |
|---|---|---|
| 0.26 | 45.2 | 1.7 |
| 0.40 | 64.0 | 2.3 |
| 0.45 | 69.7 | 2.6 |
| 0.55 | 79.7 | 3.4 |
| 0.65 | 87.7 | 4.8 |

Table 2 below sets out the calculated molecular weight distribution, in weight per cent, of various groups of alcohol products resulting from Fischer-Tropsch syntheses operated at different conditions resulting in different Schulz-Flory $\alpha$-values.

TABLE 2

| $\alpha$ | 0.4 | 0.6 | 0.65 | 0.7 |
|---|---|---|---|---|
| $CH_3OH$ | 36.00 | 16.00 | 12.25 | 9.00 |
| $C_2$ to $_4$ | 55.30 | 50.39 | 44.91 | 38.18 |
| $C_5$ to $_{11}$ | 8.67 | 31.74 | 38.60 | 44.32 |
| $C_{12}$ to $_{16}$ | 0.03 | 1.75 | 3.57 | 6.58 |
| $C_{17+}$ | 0.00 | 0.21 | 0.67 | 1.93 |

The proportion of $C_5$ to $C_{11}$ alcohols rises from about 8.7% at an $\alpha$ of 0.4 to about 39% at an $\alpha$ of 0.65.

For example, under given conditions, with a CoCu catalyst with Zn as the third co-precipitated metal, a typical $\alpha$-value of 0.4 is achieved, representing a mean $C_n$ of 2.3 and with a CoCu catalyst with Cr as the third metal, an α-value of 0.45 is achieved representing a mean $C_n$ of 2.6. In accordance with the present invention, however, with a CoCu catalyst with Mg as the third metal, an α-value of 0.65, representing a mean $C_n$ of 4.8, is achieved, showing a substantial increase in the mean molecular weight of product over that resulting from the prior art procedures.

The oxygen-containing and hydrocarbon products of the process of the first aspect of the invention have varied utilities. For example, the alcohols find especial utility as solvents and intermediates in the manufacture of esters, for example for plasticizer and lubricant use, including synthetic lubricant base stocks or lubricant additives. The esters further find utility as solvents, polymerizable monomers e.g., the (meth) acrylates, viscosity improvers, and stabilizers for vinyl chloride polymers e.g., the phosphates, and cetane improvers, e.g., the nitrates. The alcohols, especially those of $C_8$ and above, may be converted to alkoxylates, especially ethoxylates, sulphates or ether sulphates and used as surfactants. Dehydrogenation of the alcohols to aldehydes yields further useful intermediates in the manufacture of, for example, amines and acids.

The amines may be used as such, or after alkoxylation, especially ethoxylation, as surfactants. The acids may be alkoxylated, especially ethoxylated, to form surfactants or may be esterified, by mono- and/or poly-hydric alcohols to provide plasticizers and lubricant basestocks or lubricant additives. The aldehydes may be aldolized and if desired hydrogenated to form alcohols which may in turn be used as raw materials or intermediates in acid, amine, or ester manufacture.

The unsaturated hydrocarbons are valuable raw materials for use as polymerizable or oligomerizable monomers, or as reactants in the oxo process, the products of which may be hydrogenated to alcohols or aldolized to form higher molecular weight unsaturated aldehydes which may in turn be hydrogenated to form alcohols which themselves may be derivatized to yield compounds, e.g., esters, having utility as described above and as emollients in cosmetics.

The invention accordingly also provides all these products when made using the processes of and products of the preceding aspects of the invention.

The following examples illustrate the invention.

EXAMPLES 1 TO 3, CATALYST PREPARATION

EXAMPLE 1

1.21 g of cobalt(II) nitrate hexahydrate, 1.00 g of copper (II) nitrate trihydrate, and 2.13 g of manganese (II) nitrate tetrahydrate were dissolved in 8 ml of water to give an aggregate molar solution in which the atomic ratios of Co:Cu:Mn were approximately 1:1:2. 2.39 g of ammonium oxalate monohydrate (a quantity giving a molar ratio of total metal:oxalate of 1:1) were dissolved in 55 ml water and the mixed nitrate solution was poured in with vigorous stirring. Precipitation occurred immediately. The precipitate was filtered off, washed with distilled water, dried in air at 110° C., and calcined in air at 450° C. Potassium nitrate was added to a portion of the calcined material as a promoter, by adding an aqueous solution until the first sign of wetness is apparent (the incipient wetness technique). Catalysts of Co:Cu:Mn constitution 1:1:1 and 1:1:3 were prepared in the same way. TPDec observation on the oxalate indicated a mixed phase, CoCuMn, representing up to 95% of the material.

EXAMPLE 2

0.51 g of cobalt nitrate, 2.02 g of copper nitrate (using the hydrates as in Example 1), and 0.5 g of magnesium nitrate hexahydrate were dissolved in 10 ml water at 40° C. to 50° C. to give a solution in which the Co:Cu:Mg atomic ratios were approximately 1:4:1. 1.72 g of ammonium oxalate monohydrate (to give an equimolar ratio of oxalate to total metal) were dissolved in 18 ml of water at 40° C. to 50° C., and the nitrate solution, having been maintained in the same temperature range, was poured in with vigorous stirring. Immediate precipitation took place. Part of the precipitate was treated as described in Example 1, to prepare the potassium-promoted catalyst. TPDec observation on the oxalate precipitate indicated two mixed phases, of CoCu and MgCoOxCu. A catalyst of constitution Co:Cu:Mg 1:4:2.5 was prepared in the same way.

EXAMPLE 3

This example illustrates the use of an organic solvent in catalyst preparation. 3.04 g of cobalt nitrate, 2.52 g of copper nitrate, and 1.31 g of manganese nitrate (using the hydrates as in Example 1) were dissolved in 300 ml of 2-propanol to give a solution in which the atomic ratios of Co:Cu:Mn were 1:1:0.5. 3.3 g of oxalic acid dihydrate were dissolved in 120 ml of 2-propanol, and the solution poured into the solution of nitrates with vigorous stirring. Immediate precipitation yielded a slurry that was filtered off, dried in air at 110° C., and calcined in air at 450° C.

EXAMPLES 4 TO 8 ALCOHOL SYNTHESIS

Catalysts prepared as in Example 1, some unpromoted and some promoted with potassium, were activated by hydrogen reduction at 350° C. Synthesis gas, at various ratios of $H_2$ to CO, was passed over each catalyst at a GHSV of 4800 $h^{-1}$ at 60 bar. Other conditions and the results are set out in Table 3 below.

The percentage K shown in the table is the percentage by weight of potassium based on the total weight of catalyst. The composition of the three essential elements is given in atomic ratios.

"Surf CO" indicates the specific surface area of the catalyst in terms of the number of molecules of CO absorbed per g of CoCu in the catalyst.

The catalysts were maintained on-stream for typically three days without loss of catalytic activity.

TABLE 3

| Example | 4 | 5 | 6 | 7 | 8 |
|---|---|---|---|---|---|
| Co:Cu:Mn | 1:1:3 | 1:1:3 | 1:1:2 | 1:1:2 | 1:1:1 |
| % K | — | 0.3 | — | 0.1 | — |
| Surf CO × $10^{19}$ | 91 | — | 86 | — | 96 |
| $H_2$:CO | 2.1 | 1.8:1 | 1.8:1 | 1.5:1 | 1.8:1 |
| Temp, ° C. | 250 | 250 | 240 | 240 | 240 |
| Conv, CO, % | 20 | | 8 | | 10.5 |
| α to RH | 0.52 | 0.61 | 0.66 | 0.65 | 0.59 |
| α to RH= | 0.67 | 0.59 | 0.61 | 0.57 | 0.55 |
| α to ROH | 0.60 | 0.61 | 0.61 | 0.54 | 0.61 |
| Selectivity %, to $CO_2$ | 3 | 1 | 3 | 5 | 4 |
| Selectivity %, ex. $CO_2$, to | | | | | |
| RH | 68 | 23 | 21 | 20 | 25 |
| RH= | 13 | 47 | 45 | 45 | 41 |
| ROH | 19 | 30 | 34 | 35 | 34 |
| Activity μmol/g cat/min | 690 | | 440 | | 452 |

The results in Table 3 show good selectivity to alcohols and olefins and, by reference to Table 2, a good yield of material in the valuable $C_5$ to $C_{11}$ range.

EXAMPLES 9 TO 18, ALCOHOL SYNTHESIS

Catalysts prepared as in Example 2, with Co:Cu:Mg atomic ratios of 1:4:2.5, some unpromoted and some promoted with potassium, were activated by reduction with hydrogen at 350° C. Synthesis gas at various $H_2$:CO ratios was passed over the catalyst at 60 bar and 280° C. Other conditions and the results are set out in Table 4 below.

TABLE 4

| Example | 9 | 10 | 11 | 12 | 13 | 14 | 15 | 16 | 17 | 18 |
|---|---|---|---|---|---|---|---|---|---|---|
| % K | 0 | 0 | 0 | 0.1 | 0.1 | 0.3 | 0.3 | 0.3 | 0.7 | 0.7 |
| $H_2$:CO | 2:1 | 1.8:1 | 1.5:1 | 2:1 | 1.8:1 | 2:1 | 1.8:1 | 1.5:1 | 2:1 | 1.8:1 |
| GHSV $h^{-1}$ | 6600 | 6600 | 6600 | 4800 | 4800 | 4800 | 4800 | 4800 | 4800 | 4800 |
| Conv, CO, % | 7.6 | 6.4 | 3.2 | 4.0 | 2.6 | 3.8 | 3.2 | 3.1 | 3.9 | 3.4 |
| α to RH | 0.63 | 0.59 | 0.60 | 0.63 | 0.67 | 0.65 | 0.63 | 0.64 | 0.57 | 0.64 |
| α to RH= | 0.53 | 0.47 | 0.48 | 0.54 | 0.53 | 0.49 | 0.53 | 0.53 | 0.43 | 0.51 |
| α to ROH | 0.57 | 0.59 | 0.56 | 0.52 | 0.57 | 0.58 | 0.59 | 0.59 | 0.62 | 0.66 |
| Selectivity %, to $CO_2$ | 3 | 4 | 5 | 18 | 27 | 42 | 50 | 48 | 68 | 65 |
| Selectivity %, ex. $CO_2$, to | | | | | | | | | | |
| RH | 41 | 43 | 39 | 35 | 34 | 40 | 36 | 35 | 50 | 46 |
| RH= | 45 | 39 | 39 | 26 | 22 | 19 | 18 | 17 | 3 | 9 |
| ROH | 14 | 18 | 22 | 39 | 44 | 41 | 46 | 48 | 47 | 45 |

The results show that selectivity to alcohols on a basis including $CO_2$ reaches a maximum at about 0.1% by weight potassium, an unacceptable level of $CO_2$ production occurring at concentrations much above this. The α values also show valuable selectivity to $C_5$ to $C_{11}$ material.

EXAMPLES 19 AND 20

These examples examine the relationship between the proportion of mixed phase in the catalyst and selectivity to alcohols manufacture. A series of magnesium-containing catalysts and a single manganese-containing catalyst were made by the procedures described in Examples 1 and 2, and the percentage of mixed by phase determined by correlation with TPDec data. Selectivity to alcohols, determined by gas chromatography, of synthesis gas reaction catalysed by the materials was measured. (Other materials detected in the product stream included alkaness, alkenes aldehydes, $CO_2$, $H_2O$, CO, $N_2$ and He.) The results are shown in Table 5.

TABLE 5

| Example | Composition | Atomic Ratio | % Mixed Phase | Selectivity ROH % |
|---|---|---|---|---|
| Comparison | CoCuMg | 1:0:7.5 | 0 | 0 |
| 19 | CoCuMg | 1:1:2.5 | 15 | 5 |
| 20 | CoCuMg | 1:1:1.2 | 26 | 10 |
| 11 | CoCuMg | 1:4:2.5 | 64 | 21 |
| 8 | CoCuMn | 1:1:1 | 95 | 33 |

The positive correlation between mixed phase content and alcohol production is apparent.

EXAMPLE 21

This example examines the products from a reaction carried out using the same catalyst and under conditions similar to those of Example 6, resulting in selectivities very close to those found in that example, RH:20; RH=:46; ROH:32, and $CO_2$:2. The percentage by weight in each product, as analsyed by chromatography, was as follows:

TABLE 6

| $C_n$ | Alkane | Alkene | Alcohol |
|---|---|---|---|
| 1 | 17 | — | 11 |
| 2 | 18 | 36 | 25 |

TABLE 6-continued

| $C_n$ | Alkane | Alkene | Alcohol |
|---|---|---|---|
| 3 | 16 | 28 | 12 |
| 4 | 13 | 12 | 19 |
| 5 | 11 | 8 | 12 |
| 6 | 8 | 7 | 7 |
| 7 | 7 | 3 | 5 |
| 8 | 4 | 2 | 4 |
| 9 | 3 | 2 | 2 |
| 10 | 2 | 1 | 1 |
| 11 | 1 | 1 | 1 |
| 12 | 0 | 0 | 1 |

EXAMPLE 22

A Co:Cu:Mn catalyst, atomic ratios 1:1:0.5, prepared as described in Example 3, was activated by hydrogen reduction. Synthesis gas, $H_2$:CO ratio 2:1, was passed over the catalyst at 50 bar. The results are shown in Table 7.

TABLE 7

| Conversion, CO, % | 14 |
|---|---|
| α to RH | 0.61 |
| α to RH = | 0.55 |
| α to ROH | 0.63 |
| % Selectivity to $CO_2$ | 8 |
| to RH | 25 |
| to RH = | 26 |
| to ROH | 41 |

The results show good selectivity to alcohols and, by reference to Table 2, a good yield of valuable $C_5$ to $C_{11}$ material.

We claim:

1. A process for the manufacture of a catalytic composition which comprises forming a solution of a cobalt salt, a copper salt, and a salt of at least one metal selected from the group consisting of manganese and magnesium, and simultaneously precipitating the metals as oxalates from solution by the addition of oxalate ions.

2. A process as claimed in claim 1, wherein oxalate ions are provided by addition of ammonium oxalate.

3. A process as claimed in claim 1, which also comprises heat-treating the resulting oxalates.

4. The process of claim 1 where the pH of the solution is between 5 and 7.

5. The process of claim 1 wherein the cobalt, copper, and manganese are present in atomic ratios of Co:Cu:Mn within the range of 1:1 to 10:0.1 to 5.

6. The process of claim 1 wherein the cobalt, copper, and magnesium are present in atomic ratios of Co:Cu:Mg within the range of 1:1 to 10:0.1 to 10.

7. The process of claim 1 wherein the solution further contains a metal selected from the group consisting of alkali metals and alkaline earth metals.

8. The process of claim 1 wherein the solution contains potassium.

9. The process of claim wherein the cobalt, copper, and manganese are present in atomic ratios of Co:Cu:Mn within the range 1:1 to 10:0.15 to 5, and the solution further contains a total of at most 1% by weight of alkali metal and alkaline earth metal, based on the total weight of metal in the catalytic composition.

10. The process of claim 1 wherein the cobalt, copper, and manganese are present in atomic ratios of Co:Cu:Mg within the range 1:1 to 10:0:15 to 10, and the solution further contains a total of at most 1% by weight of alkali metal and alkaline earth metal, based on the total weight of metal in the catalytic composition.

11. The process of claim 5 wherein the molar proportion of the total cobalt and copper in the catalyst that is present in a mixed phase is at least 25%.

12. The process of claim 1 where the solvent comprises an organic solvent.

13. The process of claim 1 wherein the solvent comprises methanol, ethanol, acetone, or propanol.

14. The process of claim 6 wherein the molar proportion of the total cobalt and copper in the catalyst that is present in a mixed phase is at least 25%.

15. The process of claim 5 wherein the molar proportion of the total cobalt and copper in the catalyst that is present in a mixed phase is at least 50%.

16. The process of claim 5 wherein the molar proportion of the total cobalt and copper in the catalyst that is present in a mixed phase is at least 50%.

17. The process of claim 1 wherein the solution is stirred during precipitation.

18. The process of claim 1 wherein the precipitation occurs at a temperature between 40 and 60° C.

19. The process of claim 1 wherein the precipitation occurs at room temperature.

20. The process of claim 1 wherein the precipitating agent is oxalic acid.

21. The process of claim 1 wherein the precipitate is dried at a temperature of 90 to 150° C.

22. The process of claim 1 wherein the precipitate is dried at a temperature of 90 to 150° C. and then calcined at a temperature of 400 to 600° C.

23. The process of claim 1 wherein the precipitate is dried at a temperature of 90 to 150° C., then calcined at a temperature of 400 to 600° C., and then reduced with hydrogen at a temperature of 300 to 400° C.

24. The process of claim 1 wherein the salt of at least one metal selected from the group consisting of manganese and magnesium is a manganese salt.

25. The process of claim 1 wherein the salt of at least one metal selected from the group consisting of manganese and magnesium is a magnesium salt.

26. The process of claim 1 wherein the solvent comprises water.

* * * * *